(12) United States Patent
Lin et al.

(10) Patent No.: US 7,570,800 B2
(45) Date of Patent: Aug. 4, 2009

(54) METHODS AND SYSTEMS FOR BINNING DEFECTS DETECTED ON A SPECIMEN

(75) Inventors: Jason Z. Lin, Saratoga, CA (US); Xing Chu, Santa Clara, CA (US); Kenong Wu, Davis, CA (US); Sharon McCauley, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 423 days.

(21) Appl. No.: 11/300,172

(22) Filed: Dec. 14, 2005

(65) Prior Publication Data

US 2007/0133860 A1 Jun. 14, 2007

(51) Int. Cl.
*G06K 9/00* (2006.01)
(52) U.S. Cl. ...................... 382/149; 382/151
(58) Field of Classification Search .................. 382/149, 382/151
See application file for complete search history.

(56) References Cited

U.S. PATENT DOCUMENTS

| | | | |
|---|---|---|---|
| 4,579,455 A | 4/1986 | Levy et al. | |
| 5,521,987 A | 5/1996 | Masaki | |
| 5,867,590 A * | 2/1999 | Eylon | 382/151 |
| 5,991,699 A | 11/1999 | Kulkarni et al. | |
| 6,104,835 A | 8/2000 | Han | |
| 6,137,893 A * | 10/2000 | Michael et al. | 382/103 |
| 6,330,354 B1 * | 12/2001 | Companion et al. | 382/150 |
| 6,356,300 B1 * | 3/2002 | Shiba | 348/130 |
| 6,396,943 B2 * | 5/2002 | Yamashita | 382/144 |
| 6,445,199 B1 | 9/2002 | Satya et al. | |
| 6,539,106 B1 * | 3/2003 | Gallarda et al. | 382/149 |
| 6,650,779 B2 | 11/2003 | Vachtesvanos et al. | |
| 6,718,048 B1 * | 4/2004 | Kawata et al. | 382/103 |
| 6,718,526 B1 | 4/2004 | Eldredge et al. | |
| 6,735,745 B2 * | 5/2004 | Sarig | 716/4 |
| 6,748,104 B1 * | 6/2004 | Bachelder et al. | 382/151 |
| 6,771,808 B1 * | 8/2004 | Wallack | 382/151 |
| 6,804,381 B2 | 10/2004 | Pang et al. | |
| 6,829,382 B2 * | 12/2004 | Lee et al. | 382/151 |
| 6,850,646 B1 * | 2/2005 | Silver et al. | 382/199 |
| 6,855,930 B2 | 2/2005 | Okuda et al. | |
| 6,865,288 B1 | 3/2005 | Shishido et al. | |
| 6,898,318 B2 | 5/2005 | Hotta | |

(Continued)

OTHER PUBLICATIONS

U.S. Appl. No. 11/005,658, filed Dec. 7, 2004.

(Continued)

*Primary Examiner*—Bhavesh M Mehta
*Assistant Examiner*—Sean Motsinger
(74) *Attorney, Agent, or Firm*—Ann Marie Mewherter (57) ABSTRACT

Methods and systems for binning defects detected on a specimen are provided. One method includes comparing a test image to reference images. The test image includes an image of one or more patterned features formed on the specimen proximate to a defect detected on the specimen. The reference images include images of one or more patterned features associated with different regions of interest within a device being formed on the specimen. If the one or more patterned features of the test image match the one or more patterned features of one of the reference images, the method includes assigning the defect to a bin corresponding to the region of interest associated with the reference image.

45 Claims, 3 Drawing Sheets

U.S. PATENT DOCUMENTS

| | | | |
|---|---|---|---|
| 6,925,203 B1 * | 8/2005 | Tanaka | 382/151 |
| 6,930,782 B1 | 8/2005 | Yi et al. | |
| 6,947,587 B1 | 9/2005 | Maeda et al. | |
| 6,993,192 B1 * | 1/2006 | Silver et al. | 382/209 |
| 7,006,712 B1 * | 2/2006 | Silver et al. | 382/300 |
| 7,043,081 B1 * | 5/2006 | Silver et al. | 382/209 |
| 7,124,379 B2 * | 10/2006 | Buechner et al. | 716/4 |
| 7,235,411 B2 * | 6/2007 | Lim et al. | 438/5 |
| 2004/0081350 A1 * | 4/2004 | Kitamura et al. | 382/149 |
| 2004/0091142 A1 | 5/2004 | Peterson et al. | |
| 2005/0062963 A1 | 3/2005 | Yoshida et al. | |
| 2006/0215901 A1 * | 9/2006 | Nakagaki et al. | 382/149 |
| 2006/0269120 A1 * | 11/2006 | Nehmadi et al. | 382/145 |

OTHER PUBLICATIONS

U.S. Appl. No. 10/954,968, filed Sep. 30, 2004.
U.S. Appl. No. 60/738,290, filed Nov. 18, 2005.
U.S. Appl. No. 11/226,698, filed Sep. 14, 2005.
International Search Report and Written Opinion for PCT/US06/62100 mailed on Jul. 16, 2008.

* cited by examiner

METHODS AND SYSTEMS FOR BINNING DEFECTS DETECTED ON A SPECIMEN

BACKGROUND OF THE INVENTION

1. Field of the Invention

This invention generally relates to methods and systems for binning defects detected on a specimen. Certain embodiments relate to assigning a defect to a bin corresponding to a region of interest associated with a reference image if one or more patterned features proximate to the defect match one or more patterned features in the reference image.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etching, deposition, and ion implantation. Multiple semiconductor devices may be fabricated in an arrangement on a semiconductor wafer and then separated into individual semiconductor devices.

Semiconductor device design and reticle manufacturing quality are verified by different procedures before the reticle enters a semiconductor fabrication facility to begin production of integrated circuits. The semiconductor device design is checked by software simulation to verify that all features print correctly after lithography in manufacturing. Such checking is commonly referred to as "Design Rule Checking." The output of DRC can produce a potentially large set of critical points, sometimes referred to as "hot spots" on the reticle layout. This set can be used to direct a point-to-point inspector, such as a review scanning electron microscope (SEM), but this can be highly inefficient due to the number of critical points. The reticle is inspected at the mask shop for reticle defects and measured to ensure that the features are within specification. Marginal resolution enhancing technology (RET) designs not noted by simulation checks translate into electrical failures in wafer fabrication, affect yield, and possibly remain unnoticed until wafer fabrication is complete.

Methods have been invented to address the above-described needs. These methods are often referred to as "Process Window Qualification" Methods or "PWQ" Methods and are described in U.S. Patent Application Publication No. US2004/0091142 to Peterson et al., which is incorporated by reference as if fully set forth herein. These methods were extended to include using the background behind the defects found in PWQ to bin the defects. These methods are described in U.S. patent application Ser. No. 11/005,658 filed Dec. 7, 2004 by Wu et al., which is incorporated by reference as if fully set forth herein Reticle, photomask, and wafer inspection using either optical or electron beam imaging are important techniques for debugging semiconductor manufacturing processes, monitoring process variations, and improving production yield in the semiconductor industry. With the ever decreasing scale of modern integrated circuits (ICs) as well as the increasing complexity of the manufacturing process, inspection becomes more and more difficult. For example, the number of defects detected during each inspection process can be substantially large, and defects can be caused by many different mechanisms with severities ranging from disastrous impacts on product yields to trivial anomalies with no effect on product quality. The capability to separate defects of interest (DOI) from defects that are considered nuisance can mean the difference between a successful inspection and a failed attempt with useless data.

Many methodologies and technologies have been developed in attempts to classify a defect detected during inspection (e.g., performed during a semiconductor manufacturing process) as either a DOI or nuisance. One typical approach is to analyze the attributes of the defect such as size and magnitude and perform classification based on these attributes (e.g., using deterministic rules). However, there are situations in which defects with the same attributes occur at many areas of the device and only impact device yield or otherwise indicate serious problems when they occur in certain determinable regions of the device. In these situations, classification methods based on defect attributes will not be able to separate DOI in those defined regions of the device from nuisance in other regions. The size, geometry, and distribution of these potential regions for DOI, as well as the accuracy of the defect locations reported by inspection, make methods such as controlling the inspection recipe by wafer location and filtering by defect location impractical as ways to eliminate nuisances from inspection results. The only currently available reliable method for separating DOI from nuisance in these situations is by manually reviewing all of the defects detected during the inspection, which is a prohibitively time consuming process.

Another approach is to examine the appearance of defects or the appearance of the surrounding area and group the defects using a statistical approach such as nearest neighbor or neural network. There are, however, a number of limitations to statistical approaches. For example, statistical approaches identify "matches" that are not exact. Even if statistical approaches are supplemented with defect attributes, different defects may be grouped together. In addition, for certain layers, the DOI are present on particular patterns of background whereas the nuisance events are located on one or more other patterns. Statistical grouping does not accurately separate such defects. In the case of PWQ, statistical methods for binning defects based on background have been shown to have value, but they may produce binning results that are impure (in the sense that bins contain defects that are different in background) and inaccurate (in the sense that bins do not include all of the defects from the same background). For instance, the use case requires matching to precise background patterns, which cannot be performed using statistical methods.

A hybrid approach has been developed that uses both deterministic and statistical methods, which is described in U.S. patent application Ser. No. 10/954,968 filed on Sep. 30, 2004 by Huet et al., which is incorporated by reference as if fully set forth herein.

Another defect binning methodology used in PWQ and in standard defect analysis is to identify defects that repeat spatially on the specimen. A "repeater" is commonly defined as a defect that occurs at one point in a reticle. The currently methodology for finding repeaters is to look for common (x, y) locations in the defect results. This repeater technique only works in die-to-die defect detection if there are multiple die on the reticle. The repetition may be at the die level, reticle level (on wafers), or at the level of repeating patterns within the die such as repeating patterns in memory and test devices. Due to uncertainty in the locations of the defects, algorithms used to identify repeating defects require a tolerance around the defect locations. If the required tolerance is too large, false matches can result. For highly defective regions, such as are seen in PWQ and focus exposure matrices, this location uncertainty can result in "false matches" in which defects are binned as repeating when they are located on different backgrounds. False matches can also occur in systems with large defect location uncertainty. Another limitation of the current algorithms is that by relying on defect location alone, they cannot identify defects that are located on the same background but not at the same position on the wafer.

Accordingly, it would be advantageous to develop methods and systems for binning defects detected on a specimen that can be used to distinguish between DOI and nuisance defects based on the regions of the device in which the defects are located. It would also the advantageous to develop methods and systems for precisely identifying repeating defects on a specimen.

SUMMARY OF THE INVENTION

The following description of various embodiments of methods, carrier media, and systems is not to be construed in any way as limiting the subject matter of the appended claims.

One embodiment relates to a computer-implemented method for binning defects detected on a specimen. The method includes comparing a test image to reference images. The test image includes an image of one or more patterned features formed on the specimen proximate to a defect detected on the specimen. The reference images include images of one or more patterned features associated with different regions of interest within a device being formed on the specimen. If the one or more patterned features of the test image match the one or more patterned features of one of the reference images, the method includes assigning the defect to a bin corresponding to the region of interest associated with the one reference image.

In one embodiment, the different regions of interest include regions of the device in which defects of interest (DOI) may be present. In another embodiment, the different regions of interest do not include regions of the device in which nuisance defects may be present. As used herein, a region of the device in which a particular type of defect "may be present" is generally defined as a region in which defects of the particular type are potentially present or can be present. In an additional embodiment, if the one or more patterned features of the test image do not match the one or more patterned features of any of the reference images, the method includes identifying the defect as a nuisance defect.

As described above, therefore, the method may include positively identifying defects located within regions of interest. In some embodiments, however, the regions of the device in which nuisance defects may be present ("nuisance regions") are identified, and reference images for these regions may be compared to a test image as described above. If the one or more patterned features of the test image match the one or more patterned features of any of these nuisance regions, then the method includes identifying the defect as a nuisance defect. In this manner, the methods described herein can be used to positively identify potential DOI, and defects that do not match any of the reference images can be identified as nuisance. Alternatively, the methods described herein can be used to positively identify the nuisance defects, and defects that do not match any of the reference images can be identified as potential DOI.

However, in some embodiments, both of these modes can be combined in a single computer-implemented method. For example, these two different approaches (identifying a defect as a nuisance defect if the one or more patterned features of the test image do not match the one or more patterned features of any of the reference images and identifying a defect as a nuisance defect if the one or more patterned features of the test image match the one or more patterned features of a reference image corresponding to a nuisance region) can be combined into a single method to obtain optimal results.

In one such embodiment, the reference images include images of one or more patterned features associated with regions of the device in which nuisance defects may be present. If the one or more patterned features of the test image match the one or more patterned features of one of the reference images associated with the regions of the device in which nuisance defects may be present, the method includes identifying the defect as a nuisance defect. As described above, the reference images may also include images of one or more patterned features associated with different regions of interest within a device being formed on the specimen. In addition, if the one or more patterned features of the test image match the one or more patterned features of one of the reference images, the method includes assigning the defect to a bin corresponding to the region of interest associated with the one reference image. Therefore, in some such embodiments, if the one or more patterned features of the test image do not match the one or more patterned features of any of the reference images (e.g., reference images associated with nuisance defects and reference images associated with different regions of interest), the method includes identifying the defect as a nuisance defect.

In one embodiment, the test image includes an image of the defect. In a different embodiment, the test image is acquired at a location on the specimen spaced from the defect at which the one or more patterned features are located and at which additional defects are not located.

In some embodiments, the method includes identifying the regions of interest containing potentially problematic portions of the design of the device based on results of the assigning step. In a further embodiment, the method includes identifying potentially problematic processes used to fabricate the specimen based on results of the assigning step.

In some embodiments, if the one or more patterned features of the test image match the one or more patterned features of one of the reference images, the method includes determining if the defect is a repeating defect (e.g., classifying or confirming the defect as a defect that repeats in a pattern, die, or reticle). In another embodiment, the method includes classifying the defect based on one or more attributes of the defect. In an additional embodiment, the method includes classifying the defect based on one or more attributes of the defect and one or more attributes of the one or more patterned features formed on the specimen proximate to the defect.

In one embodiment, the method includes sampling the defects detected on the specimen for additional processing based on results of the assigning step. In another embodiment, the method includes locating additional instances of the one or more patterned features proximate to the defect in the device. In an additional embodiment, the method includes locating additional instances of the one or more patterned features proximate to the defect on the specimen.

In one embodiment, the method includes acquiring the test image by optical inspection. In another embodiment, the method includes acquiring the test image by electron beam inspection. In other embodiments, the method includes acquiring the test image by electron beam review (e.g., scanning electron microscopy (SEM) review). In yet another embodiment, the method includes acquiring the test image by an aerial image projection technique.

In some embodiments, the method is performed during inspection of the specimen. In other embodiments, the method is performed using the test image acquired during inspection of the specimen. In other embodiments, the method is performed during review of the defects (e.g., on a review station that revisits sites found by inspection of the specimen). In other embodiments, the method includes acquiring the test image by analyzing design data for the device being formed on the specimen.

In some embodiments, the method may performed using pattern matching alone. In other embodiments, the method is performed in conjunction with statistical methods performed on the test image (e.g., to improve performance of the method). Each of the embodiments of the method described above may include any other step(s) of any other method(s) described herein.

Another embodiment relates to a different method for binning defects detected on a specimen. The method includes comparing a first test image to a second test image. The first test image includes an image of one or more patterned features formed on the specimen proximate to a first defect detected on the specimen. The second test image includes an image of one or more patterned features formed on the specimen proximate to a second defect detected on the specimen. If the one or more patterned features in the first and second test images match, the method includes assigning the first and second defects to the same bin. Although embodiments of this method are described with respect to a first test image and a second test image corresponding to a first defect and a second defect, respectively, it is to be understood that the method may include comparing the first test image to more than one other test image (e.g., at least two test images).

In one embodiment, the first and second test images include images of the first and second defects, respectively. In a different embodiment, the first and second test images are acquired at locations on the specimen spaced from the first and second defects, respectively, at which the one or more patterned features are located and at which additional defects are not located.

In one embodiment, the method includes identifying potentially problematic portions of the design of a device being formed on the specimen based on results of the assigning step. In another embodiment, the method includes identifying a sample of the defects detected on the specimen to be reviewed based on results of the assigning step. In a further embodiment, the method includes identifying potentially problematic processes used to fabricate the specimen based on results of the assigning step.

In an additional embodiment, if the one or more patterned features in the first and second test images match, the method includes determining if the first and second defects are repeating defects (e.g., classifying or confirming the defects as defects that repeat in a pattern, die, or reticle). In some embodiments, the method includes classifying the first and second defects based on one or more attributes of the first and second defects, respectively. In a further embodiment, the method includes classifying the first and second defects based on one or more attributes of the first and second defects, respectively, and one or more attributes of the one or more patterned features proximate to the first and second defects, respectively. In some embodiments, the method includes creating a subset of the defects based on locations of the defects within a die formed on the specimen or locations of the defects on the specimen and classifying the subset based on one or more attributes of the one or more patterned features proximate to the defects within the subset. In some embodiments, the method includes using the one or more patterned features proximate to the defects in a simulation of design data for a device being formed on the specimen to classify the defects.

In one embodiment, the method includes acquiring the first and second test images by optical inspection. In a different embodiment, the method includes acquiring the first and second images by electron beam inspection. In other embodiments, the method includes acquiring the first and second test images by electron beam review (e.g., SEM review). In yet another embodiment, the method includes acquiring the first and second test images by an aerial image projection technique.

In some embodiments, the method is performed during inspection of the specimen. In other embodiments, the method is performed using the first and second test images acquired during inspection of the specimen. In different embodiments, the method is performed during review of the defects (e.g., on a review station that revisits sites found by inspection of the specimen). In other embodiments, the method includes acquiring the first and second test images by analyzing design data for the specimen.

In some embodiments, the method may be performed using pattern matching alone. In other embodiments, the method is performed in conjunction with statistical methods performed on the first and second test images (e.g., to improve performance). Each of the embodiments of the method described above may include any other step(s) of any other method(s) described herein.

An additional embodiment relates to a carrier medium. The carrier medium includes program instructions executable on a computer system for performing a method for binning defects detected on a specimen. The method includes comparing a test image to reference images. The test image includes an image of one or more patterned features formed on the specimen proximate to a defect detected on the specimen. The reference images include images of one or more patterned features associated with different regions of interest within a device being formed on the specimen. If the one or more patterned features of the test image match the one or more patterned features of one of the reference images, the method includes assigning the defect to a bin corresponding to the region of interest associated with the one reference image. The carrier medium may be further configured as described herein.

A further embodiment relates to a system configured to bin defects detected on a specimen. The system includes an inspection subsystem configured to acquire a test image of one or more patterned features formed on the specimen proximate to a defect detected on the specimen. The system also includes a computer subsystem and a carrier medium that includes program instructions executable on the computer subsystem for comparing the test image to reference images. The reference images include images of one or more patterned features associated with different regions of interest within a device being formed on the specimen. If the one or more patterned features of the test image match the one or more patterned features of one of the reference images, the program instructions are also executable on the computer subsystem for assigning the defect to a bin corresponding to the region of interest associated with the one reference image. In one embodiment, the inspection subsystem is also configured to acquire the reference images. Each of the embodiments of the system described above may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer, a photomask, or a reticle. However, it is to be understood that the methods, carrier media, and systems described herein may be used for binning defects detected on any other specimen on which defects in certain areas on the specimen are of interest and defects in other areas on the specimen are not of interest.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

The terms "reticle" and "photomask" are used interchangeably herein. A reticle generally includes a transparent substrate such as glass, borosilicate glass, and fused silica having a layer of opaque material formed thereon. The opaque regions may be replaced by regions etched into the transparent substrate. Many different types of reticles are known in the art, and the term reticle as used herein is intended to encompass all types of reticles.

The terms "first" and "second" are used herein to differentiate between different defects, test images, etc. The terms "first" and "second" are not used to indicate temporal, spatial, or preferential characteristics of the defects, test images, etc.

The method embodiments described herein include new methodology for using pattern matching technology to identify the neighboring context of a defect. The neighboring context of the defect can then be used to classify the defects as being located or not being located in one of the regions corresponding to a potential defect of interest (DOI). In addition, the neighboring context of a defect and its location within the context (i.e., defect location relative to the context) may be used to assist in the correct classification of the defect. This technique has additional applications in areas of Process Window Qualification (PWQ), finding similar defects for tuning sensitivity, and the identification of repeating defects.

The new methodology may be generally referred to as "context based binning" (CBB). The term "context" as used herein refers to one or more patterned features located proximate to a defect. In embodiments described herein, the context is defined by one or more patterned features printed on the specimen proximate to a location of a defect. However, the context may also or alternatively be defined by one or more patterned features in design data proximate to the location of a defect in design data space.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
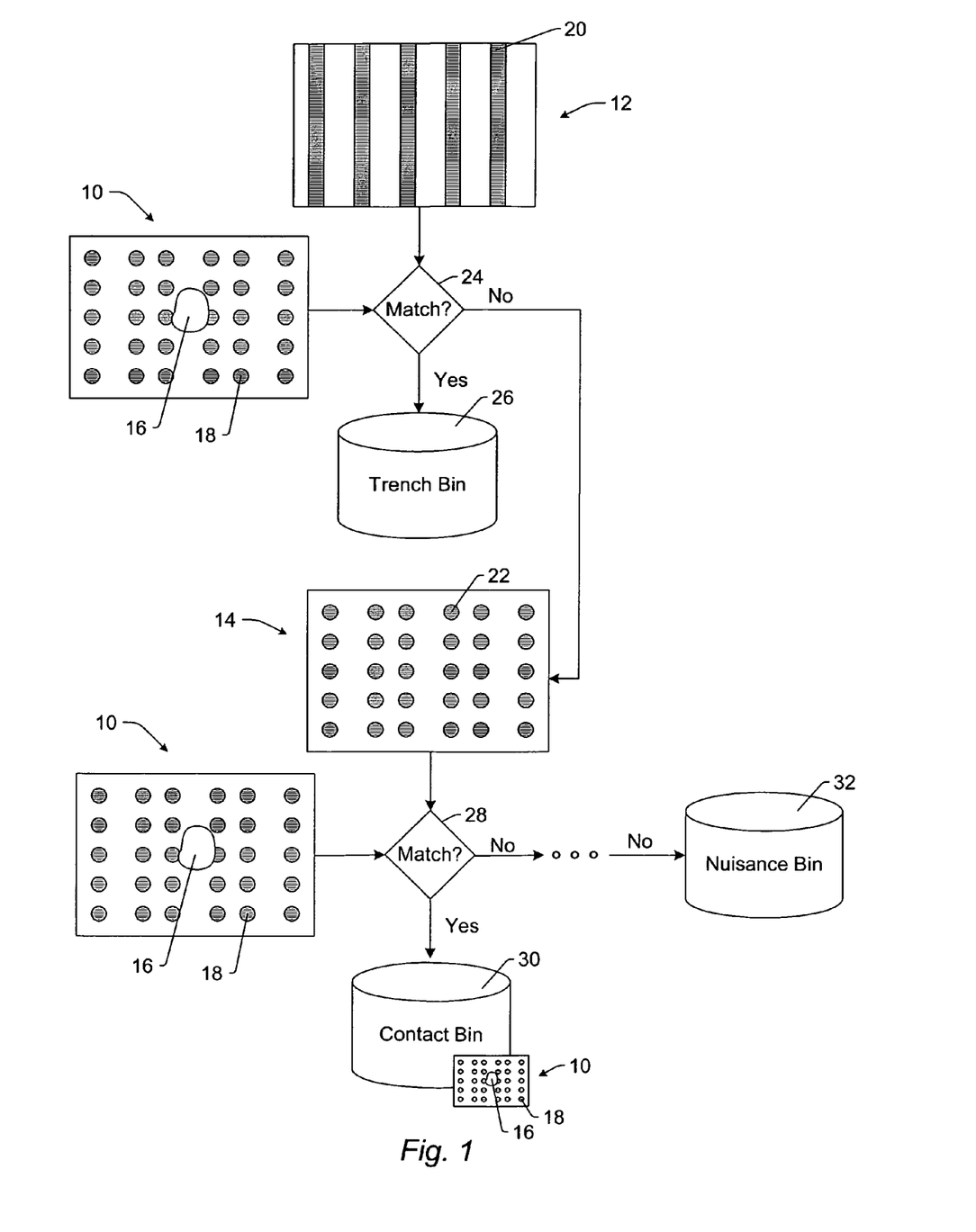
FIGS. 1-2 are schematic diagrams illustrating various embodiments of a computer-implemented method for binning defects detected on a specimen.
Figure 2:
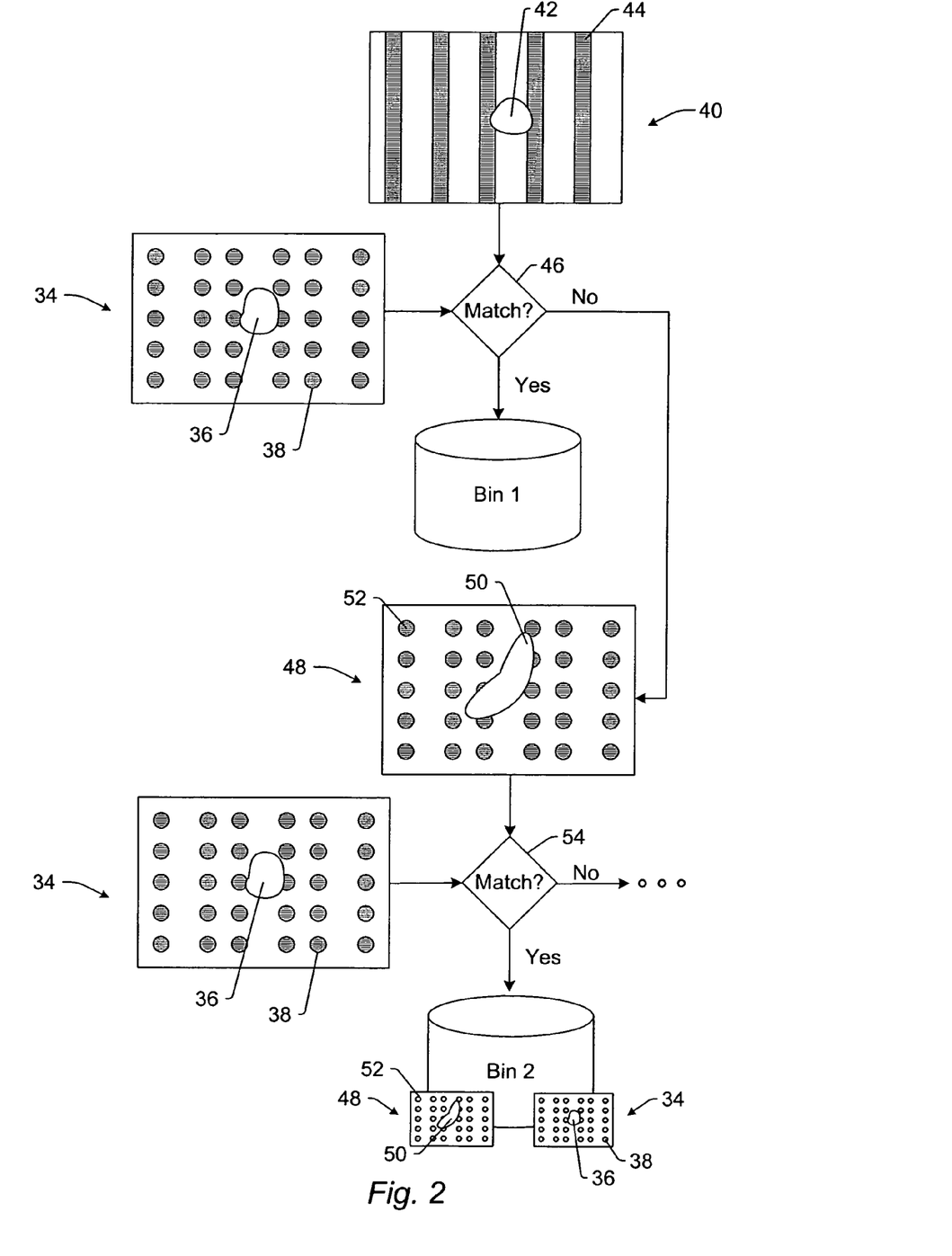

FIGS. 1-2 illustrate various embodiments of a computer-implemented method for binning defects detected on a specimen (CBB methods). In general, in the methods described herein, after a defect is detected during inspection, an image of the neighboring region of the defect is compared to reference images or reference "templates" using pattern matching technology. If a positive match is found, then the defect is identified as being located in the region of the device corresponding to the reference image that its neighboring region matches and is identified as a potential DOI or a nuisance defect.

In particular, the method shown in FIG. 1 includes comparing a test image to reference images. For example, the method may include comparing test image 10 to reference images 12 and 14. It is noted that the test and reference images illustrated and described herein are not meant to demonstrate any particular type of image that can be used in the methods described herein. In addition, it is noted that the test and reference images illustrated and described herein are provided merely to promote understanding of the methods described herein and are not meant to illustrate any particular type of defect that may be detected on a specimen or any particular type of patterned features that may be printed on a specimen or included in a device design. Obviously, the patterned features and defects illustrated in the test and reference images will vary depending on the device design, the types of defects that are caused by the process or processes performed on the specimen prior to inspection, and interactions between the device design and the process or processes performed on the specimen prior to inspection.

Test image 10 includes an image of one or more patterned features formed on a specimen proximate to a defect detected on the specimen. In one embodiment, test image 10 includes an image of defect 16 detected on the specimen and patterned features 18 formed on the specimen proximate to defect 16. In some embodiments, test image 10 may be acquired by a computer subsystem configured to perform the computer-implemented method. For example, the computer subsystem may be configured to acquire the test image from an inspection subsystem to which the computer subsystem is coupled by a transmission medium (e.g., a data link). Therefore, the computer subsystem and the inspection subsystem may or may not be included in the same system. Such a computer subsystem and inspection subsystem may be further configured as described herein. In this manner, the test image may be acquired in the computer-implemented methods described herein without performing inspection of the specimen.

In other embodiments, the computer-implemented method may include inspecting the specimen. In one such embodiment, the method includes acquiring the test image by optical inspection. In a different embodiment, the method includes acquiring the test image by electron beam inspection. Optical and electron beam inspection may be performed as described further herein using a system configured as described herein. In another embodiment, the computer-implemented method may include reviewing the defects. In one such embodiment, the method includes acquiring the test image by electron beam review. Electron beam review may be performed using any appropriate review process or system known in the art. In other embodiments, the method includes acquiring the test image by an aerial image projection technique. Such embodiments may be particularly useful for a specimen such as a reticle. The aerial image projection technique may be performed using any appropriate aerial imaging process or system known in the art. Examples of suitable methods and systems for aerial imaging that can be used in the methods and systems described herein are illustrated in U.S. Patent Application Publication No. US2004/0091142 to Peterson et al., which is incorporated by reference as if fully set forth herein.

Test image 10 may be a patch image of the specimen. However, test image 10 may be any other image of the specimen generated by inspection (e.g., a swath image or an image of the specimen acquired during inspection before a defect is detected on the specimen) or another imaging process (e.g., review). In addition, test image 10 may have any suitable image format known in the art. In other words, the methods described herein are not limited by the type of images or image data that can be used in the methods. Preferably, the one or more patterned features formed on the specimen proximate to the defect are imaged in test image 10 with sufficient resolution such that pattern matching of the one or more patterned features can be performed as described herein.

As described above, the test image may include an image of the defect. In other words, the test image may be acquired at the location of the defect on the specimen. In a different embodiment, however, the test image is acquired at a location on the specimen spaced from the defect at which the one or more patterned features are located and at which additional defects are not located. In other words, the test image may not include an image of the defect. Such an embodiment may be advantageous in instances such as when the location of the defect on the specimen is so defective that an image acquired at that location cannot be used for pattern matching. In such instances, during the detection of the defect, a corresponding image from an adjacent die or cell may be acquired. This corresponding image preferably contains the same pattern but not the defect and therefore can be used for pattern matching as described herein with relatively high accuracy. The location at which the corresponding image is acquired may be determined in any manner known in the art (e.g., based on the design of the device, the layout of the dies on the specimen, etc.)

In yet another embodiment, the method may include acquiring the test image by analyzing design data for the device being formed on the specimen. For instance, the location of the defect with respect to the design data may be determined. Examples of methods and systems for determining the location of a defect in design data space are illustrated in U.S. Patent Application Ser. No. 60/738,290 by Kulkarni et al., filed on Nov. 18, 2005, which is incorporated by reference as if fully set forth herein. Once the location of the defect in design data space has been determined, the design data proximate to the location may be used to simulate one or more patterned features formed on the specimen proximate to the defect. The simulation may be performed as described further herein. In this manner, the test image may not include an image acquired by inspection, review, etc. Instead, the test image may include simulated image data. In other embodiments, the test image may include the design data proximate to the location of the defect in design data space. In other words, the test image may not actually include image data, and the methods described herein may not be performed with a rendered image.

Reference images 12 and 14 include images of one or more patterned features associated with different regions of interest within a device being formed on the specimen. In particular, reference image 12 includes an image of patterned features 20 associated with one region of interest within a device being formed on the specimen, and reference image 14 includes an image of patterned features 22 associated with another region of interest within the device being formed on the specimen.

As shown in FIG. 1, patterned features 20 in reference image 12 are trench features formed on the specimen. Therefore, reference image 12 may be associated with a trench region of interest within a device being formed on the specimen. In addition, patterned features 22 in reference image 14 are contact features formed on the specimen. As such, reference image 14 may be associated with a contact region of interest within a device being formed on the specimen. In one embodiment, the different regions of interest include regions of the device in which DOI may be present. In this manner, the methods described herein are based on the assumption that the regions of interest in which potential DOI may be located have unique patterns that are discernable in optical or electron beam images. These patterns are identified and used as the reference templates for pattern matching. In addition, the different regions of interest may not include regions of the device in which only nuisance defects may be present.

Although only two reference images are shown in FIG. 1, it is to be understood that the test image may be compared to any number of reference images (i.e., two or more reference images). For instance, the number of reference images used in the method shown in FIG. 1 may be equal to the number of regions of interest within the device being formed on the specimen (e.g., each reference image corresponds to a different region of interest such as a gate region, a source/drain region, a contact region, an interconnect or trench region, etc.).

Reference images 12 and 14 may be acquired in a number of different manners. As described above, each reference image may correspond to a different region of interest. Therefore, a reference image may be acquired for each different region of interest within the device being formed on the specimen.

In one embodiment, the reference images may be acquired by imaging a specimen on which the regions of interest are formed. For instance, the design of the device may be used to estimate a location of a region of interest on a specimen. An inspection subsystem and/or the specimen may be positioned such that the inspection subsystem can acquire an image (e.g., a patch image) at the estimated location. To verify that an image has been acquired at a location within the region of interest, the image may be compared to the design (e.g., a simulated image that illustrates how the design will be printed on the specimen, which may be generated using methods and systems described in U.S. patent application Ser. No. 11/226, 698 filed Sep. 14, 2005 by Verma et al., which is incorporated by reference as if fully set forth herein). If one or more patterned features appear in both the image and the design for the region of interest, then the image may be verified as being acquired in the region of interest. Additional instances of this pattern may be found in the simulation data. In addition, the reference images may include images of the regions of interest in which no defects are present. For instance, after an image of a region of interest has been acquired by the inspection subsystem, a defect detection algorithm or method may be used to determine if a defect is present in the image. If a defect is present in the image, the inspection subsystem may acquire a different image at another location in the region of interest, and the steps described above may be performed until a suitably defect free reference image has been acquired.

In addition, more than one reference image may be acquired for each region of interest as described above. Therefore, in some embodiments, the method may include comparing a test image to multiple reference images for each region of interest. More than one reference image may be used for the comparison to verify matching of the one or more patterned features in the test and reference images or to increase the accuracy of the comparison results.

In another embodiment, the reference images may be acquired by simulation. For instance, the method may include generating a simulated image of each of the regions of interest using the design data as input. The simulated images preferably illustrate how each of the regions of interest will be formed on the specimen and will appear in an image acquired by inspection. Therefore, the simulated images may be similar to the test images that are acquired for the specimen except that the simulated images will not include images of defects. Generating the simulated images, therefore, preferably uses one or more models (e.g., a lithography model, an etch model, a chemical-mechanical polishing model, etc.) for the processes that will be performed on the specimen prior to inspection. Such simulations may be performed using any suitable method, algorithm, or software known in the art such as PROLITH, which is commercially available from KLA-Tencor, San Jose, Calif.

The type of reference image that is used for a particular binning method may vary depending on, for example, the characteristics of the specimen, the process or processes used to form the specimen, and the characteristics of the inspection system used to acquire the test images. For instance, if the inspection is performed after a number of processes have been performed on the specimen, a reference image that is acquired by imaging a specimen may be more suitable for comparison to test images since the accuracy of the simulated image may decrease as the number of processes that are simulated increases. In addition, a reference image that is acquired by imaging a specimen may be used if a model for a process performed on the specimen has not been developed or is not available. In another example, if the characteristics of the inspection system and the characteristics of the specimen result in test images that include defects and patterned features on more than one level of the specimen (e.g., due to a relatively transparent uppermost layer being formed on the specimen), a reference image that is acquired by imaging a similarly processed specimen may be more similar to the corresponding test image than a reference image that is acquired by simulation.

Acquiring the reference images in the embodiments described above may be performed manually, automatically, or semi-automatically (e.g., user-assisted). In one embodiment of a manual method for acquiring the reference images, a user may select the pattern of interest from clips collected in a preliminary inspection. Alternatively, the user may select the pattern from a representation of design data such as GDS data that matches the location of a defect. The user may indicate whether the matching patterns can have the same geometry flipped or rotated, or if the match must be in the same orientation as the original. The user identifies events located within the selected patterns to be false events or real events of some level of interest. The user may also assign a classification code to the pattern. The methods and systems described herein may then accept the pattern and use the pattern as described further herein.

Acquiring the reference images as described above may be performed by the computer-implemented methods described herein or by a different computer-implemented method. Therefore, the methods described herein may include acquiring the reference images by performing one or more of the steps described above or by acquiring the reference images from results (e.g., stored in a storage medium) produced by a different computer-implemented method. Furthermore, acquiring the reference images as described above may be performed once for each level of the design that will be inspected during the manufacture of the device. However, additional reference images may be acquired periodically after initial set up (e.g., during periodic maintenance or calibration) such that variations between the test and reference images over time (e.g., caused by temporal variations in the process or processes used to fabricate the specimen) do not decrease the accuracy of the method.

Comparing the test image and the reference images includes determining if the one or more patterned features, of the test image match the one or more patterned features of the reference images. In addition, in some embodiments, comparing the test image and the reference images includes determining if all of the patterned features in the test image match all of the patterned features of the reference images. In other embodiments, comparing the test image and the reference images includes determining if all of the patterned features in the test image match at least some of the patterned features of the reference images. Such an embodiment may be suitable if the reference images are images of a larger area in the region of interest than the test image.

In one example, as shown in step 24 of the method shown in FIG. 1, patterned features 18 of test image 10 are compared to patterned features 20 of reference image 12 to determine if patterned features 18 of test image 10 match patterned features 20 of reference image 12. If the one or more patterned features of the test image match the one or more patterned features of the reference image, the method includes assigning the defect to a bin corresponding to the region of interest associated with the reference image. For example, if patterned features 18 of test image 10 match patterned features 20 of reference image 12, the method includes assigning defect 16 to trench bin 26 corresponding to the trench region of interest associated with reference image 12.

Pattern matching technologies have been used in many different applications. Some examples of currently available pattern matching techniques include summing of the squares of the differences (SSD), normalized cross correlation (NCC), as well as feature extraction and then feature based matching. Examples of SSD methods are illustrated in U.S. Pat. Nos. 4,579,455 to Levy et al., 6,930,782 to Yi et al., and 6,947,587 to Maeda et al., which are incorporated by reference as if fully set forth herein. Examples of NCC methods are illustrated in U.S. Pat. Nos. 5,521,987 to Masaki and 6,865,288 to Shishido et al., which are incorporated by reference as if fully set forth herein. Examples of feature extraction methods are illustrated in U.S. Pat. Nos. 6,104,835 to Han, 6,650,779 to Vachtesvanos et al., 6,804,381 to Pan et al., and 6,855,381 to Okuda et al., which are incorporated by reference as if fully set forth herein. For techniques that are sensitive to image brightness/contract such as SSD, image brightness/contrast correction schemes have also been developed such as the gray level correction (GLC) method. Examples of methods that can be used for gray level correction are illustrated in U.S. patent application Publication No. 2005/0062963 by Yoshida et al., which is incorporated by reference as if fully set forth herein. Such technologies have been used in inspection tools for tasks such as specimen alignment and field/die registration. The methods described herein, however, are the first applications in which pattern matching technology is used to identify the neighboring context of a defect to thereby aid in the classification of the defect.

If the patterned features of test image 10 match the patterned features of reference image 12, additional test images (not shown) may be compared to the reference images as described herein. However, as clearly shown in FIG. 1, the patterned features of test image 10 and reference image 12 do not match. Therefore, the method includes comparing test image 10 to a different reference image.

For example, as shown in step 28 of the method shown in FIG. 1, test image 10 is compared to reference image 14 to determine if patterned features 18 of test image 10 match patterned features 22 of reference image 14. If the patterned features of the test image match the patterned features of the reference image, the method includes assigning the defect to a bin corresponding to the region of interest associated with reference image 14. For example, if patterned features 18 of test image 10 match patterned features 22 of reference image 14, the method includes assigning defect 16 to contact bin 30 corresponding to the contact region of interest associated with reference image 14. In this case, as shown in FIG. 1, the patterned features of test image 10 and reference image 14 do match. Therefore, defect 16 included in test image 10 is assigned to contact bin 30. The method may then include comparing additional test images to the reference images.

If the patterned features of test image 10 do not match the patterned features of reference images 12 and 14, the method may include comparing test image 10 to additional reference images (not shown) until a match is found or the test image has been compared to all of the reference images. In some embodiments, the reference images are not associated with regions of the device in which only nuisance defects may be present. Therefore, if the one or more patterned features of the test image do not match the one or more patterned features of any of the reference images, the method may include identifying the defect as a nuisance defect. In one such embodiment, a defect identified as a nuisance defect may be assigned to nuisance bin 32. However, a defect and the test image of the defect identified as a nuisance defect may also be discarded or otherwise filtered from other test images.

As described above, therefore, the method may include positively identifying the defects located within regions of interest. In some embodiments, however, the regions of the device in which nuisance defects may be present ("nuisance regions") are identified, and reference images for these regions may be compared to a test image as described above. If the one or more patterned features of the test image match the one or more patterned features of any of these nuisance regions, then the method includes identifying the defect as a nuisance defect. In this manner, the methods described herein can be used to positively identify potential DOI, and defects that do not match any of the reference images can be identified as nuisance. Alternatively, the methods described herein can be used to positively identify the nuisance defects, and defects that do not match any of the reference images can be identified as potential DOI.

However, in some embodiments, both of these modes can be combined in a single computer-implemented method. For example, these two different approaches (identifying a defect as a nuisance defect if the one or more patterned features of the test image do not match the one or more patterned features of any of the reference images and identifying a defect as a nuisance defect if the one or more patterned features of the test image match the one or more patterned features of a reference image corresponding to a nuisance region) can combined into a single method to obtain optimal results.

In one such embodiment, the reference images include images of one or more patterned features associated with regions of the device in which nuisance defects may be present. If the one or more patterned features of the test image match the one or more patterned features of one of the reference images associated with the regions of the device in which nuisance defects may be present, the method includes identifying the defect as a nuisance defect. In some such embodiments, if the one or more patterned features of the test image do not match the one or more patterned features of any of the reference images (e.g., reference images associated with regions of interest and reference images associated with regions of the device in which nuisance defects may be present), the method includes identifying the defect as a nuisance defect.

Although the method is described above with respect to a test image for a defect, it is to be understood that the method may be performed for different test images of different defects to determine if the different defects are located within regions of interest in the device. The method may be performed for some of the defects detected on a specimen or all of the defects detected on the specimen.

In one embodiment, the method is performed during inspection of the specimen. In this manner, the reference images described above may be used in-line during inspection to set a defect attribute or defect classification. In another embodiment, the method is performed during review of the defects. In this manner, the reference images may be used in-line during review to set a defect attribute or defect classification. For example, the method may be performed on a review station by revisiting sites found by inspection. This matching may be performed using only pattern matching.

In another embodiment, the method may be performed in conjunction with statistical methods performed on the test image (e.g., to improve performance). In this manner, statistical methods (possibly in combination with attribute-based rules) are used in conjunction with pattern matching. In an alternative embodiment, the method is performed using the test image acquired during inspection of the specimen. For example, the reference images may be used immediately for comparison to a set of test images collected in an earlier inspection. In such embodiments, the pattern matching may be performed alone or with other classification methodologies. In addition, the method may be performed off-line if enough inspection data is retained (e.g., available for use in the methods described herein). In another alternative, the reference images may be used to identify other instances of the pattern in the design data. In this case, pattern matching may be assisted by other applications such as design rule checking (DRC) algorithms.

The CBB method embodiments described herein have a number of advantages over prior art methods for separating DOI and nuisance defects. For instance, there are many powerful applications in which the CBB methodology can be used. In one example, the methodology can be used as a filtering tool to eliminate defects not from any pre-defined regions of interest from the population of defects detected on the specimen so that inspection is focused and efficient. In contrast, some previous attempts at filtering DOI and nuisance defects involve inspecting only areas on the specimen corresponding to regions of interest. However, the size and distribution of the regions of interest on the specimen and the accuracy with which the inspection system can be positioned above the regions of interest limit the usefulness of this method and the accuracy of the defect filtering.

Another attempt to filter DOI and nuisance defects involves changing the defect detection parameters (e.g., threshold) dynamically (e.g., in real time) based on positions on the specimen at which the inspection data was acquired and the regions of interest that are supposed to be formed at the positions on the specimen. Here again, however, the accuracy with which the inspection system can determine the positions on the specimen and the accuracy of the locations at which the regions of interest are formed on the specimen limit the usefulness and accuracy of this method.

In the methods described herein, however, all of the defects detected on a specimen can be identified as potential DOI or nuisance regardless of the position at which the defects were detected on the specimen and the positional accuracy of the inspection system since the defects can be classified as DOI or nuisance based on their neighboring context. Therefore, inspection can be performed across the entire surface of the specimen without regard to the locations of the regions of interest on the specimen. In other words, inspection can include acquiring inspection data across regions of interest and regions not of interest on the specimen. In addition, defect detection can be performed with the same data processing parameters (e.g., threshold) regardless of the position on the specimen at which the inspection data was acquired. Consequently, the methods described herein greatly simplify the inspection process itself and reduce the required performance capability of the inspection system while also increasing the accuracy with which defects can be separated into DOI and nuisance.

In another instance, the CBB methodology may be used as a classification tool to assign defects into different bins based on their neighboring context. In contrast, currently available automatic defect classification (ADC) schemes based on defect attributes and defect features do not address the fact that sometimes where a defect is located is more important than the characteristics of the defect itself. The CBB methodology described herein fills this important gap in many cases. In particular, one fundamental element of the methods described herein is that the neighboring context of the defects is treated as an important integral part of the defect. In other words, this neighboring context is treated as if it is just as important as, if not more important than, any other attributes of the defects such as size and magnitude. The CBB methods described herein, therefore, advantageously use the neighboring context of the defect to identify its location (which region of interest it is located within) and thus assist in the correct classification of the defect. In particular, the methods described herein use pattern matching technology to identify the neighboring context of the defect (i.e., the region of interest of the device design in which the defect is located) as well as its location within the context (i.e., its location relative to the context).

Using pattern matching technology also provides the CBB methodology described herein with flexibility and robustness that other attribute based classification schemes do not have even if these other schemes derive attributes not only from the defect but also the neighboring region of the defect. For instance, in methods that derive attributes such as feature vectors of the neighboring context of a defect, attributes for patterned features that do not "look alike" may be assigned the same attributes. However, the methods described herein differentiate the defects based on what the one or more patterned features proximate to the defect "look like." Therefore, pattern matching as described herein may be used as a general extension of the "Defects Like Me" application, which is described in U.S. patent application Ser. No. 11/005,658 filed Dec. 7, 2004 by Wu et al., which is incorporated by reference as if fully set forth herein. Such differences between the method embodiments described herein and previously used methods may be particularly advantageous since two patterned features that have the same general shape but are oriented in different directions may not be differentiated by currently used methods. However, such patterned features can be differentiated by the methods described herein since pattern matching is performed based on how the patterned features appear in images.

Using pattern matching technology as described herein, therefore, provides the ability to more precisely determine the classification of a defect. In one particular example, the methods described herein are more accurate than other currently used background based binning methods in that the methods described herein find more correct matches than using feature vectors derived from the background. For PWQ applications, pattern matching can also be used to find additional instances of weak features in the device design that cannot be found by other methods.

Furthermore, pattern matching as described herein may be used to assist in identifying repeating defects and systematic defects. In addition, pattern matching can be used to avoid misidentification of repeating defects. For instance, the methods described herein may be used to supplement the identification of repeating defects, where "repeating" is defined as either a repetition in the die or in the reticle or a repetition in the pattern. In one such embodiment, if the one or more patterned features of the test image match the one or more patterned features of one of the reference images, the method includes determining if the defect is a repeating defect (e.g., a defect that repeats in a pattern, die, or reticle). In this case, candidate repeaters are validated or confirmed using pattern matching. In this manner, pattern matching can also extend the capability of the repeater algorithms and methods to find defects that have the same geometry but are located at different positions on the specimen. These systematic defects are increasing in importance in determining wafer yield.

Binning of the defects as described above effectively separates the defects detected on a specimen into groups of defects that are located in different regions of interest in the device being formed on the specimen. Defects that are located in the regions of interest are, therefore, potential DOI. The method may also include determining if the potential DOI are actually DOI or "real" DOI by classifying the defects.

In some embodiments, the method includes classifying the defect based on one or more attributes of the defect. The attribute(s) of the defects may include any defect attribute(s) that can be used for classification such as size, magnitude, shape, orientation, etc. In another embodiment, the method includes classifying the defect based on one or more attributes of the defect and one or more attributes of the one or more patterned features formed on the specimen proximate to the defect. In this manner, the defects may be classified based not only on the attribute(s) of the defects but also on the attribute(s) of any patterned features located on the specimen proximate to the defect.

Any method known in the art for classifying defects based on one or more attributes of the defects possibly in combination with one or more attributes of patterned features formed on the specimen proximate to the defects may be used in the methods described herein. Examples of methods for classifying defects that may be used in the methods described herein are illustrated in U.S. Pat. No. 6,104,835 to Han, which is incorporated by reference as if fully set forth herein. Additional examples of methods for analyzing defect data are illustrated in U.S. Pat. Nos. 5,991,699 to Kulkami et al., 6,445,199 to Satya et al., and 6,718,526 to Eldredge et al., which are incorporated by reference as if fully set forth herein. The methods described herein may include any steps described in these patents.

In some embodiments, the method includes identifying the regions of interest containing potential problematic portions of the design of the device based on results of the assigning of the defects into bins. For example, the number of defects assigned to bins associated with the different regions of interest may indicate that one region of interest is more prone to systematic defects than another region of interest. Therefore, the results of the binning step may be used to identify which regions of interest exhibit pattern-dependent defects. In this manner, the results of the binning step may be used to identify the region or regions of interest in the device design that are potentially more problematic (e.g., more prone to systematic defects). Each of these steps may be performed automatically by the computer-implemented methods described herein.

In another embodiment, the method includes locating additional instances of the one or more patterned features proximate to the defect in the device. In a further embodiment, the method includes locating additional instances of the one or more patterned features proximate to the defect on the specimen. In this manner, the method may include searching in the device design or the inspection data for the specimen based on the patterned feature(s) proximate to a defect to identify additional instances of the patterned feature(s). Searching for and identifying these additional instances of the patterned feature(s) may be used to determine if all instances of the patterned feature(s) in the device or printed on the specimen are proximate to defects or the same type of defects. In this manner, multiple instances of the patterned feature(s) may be examined to determine if a defect detected proximate to at least one instance of the patterned feature(s) is repeatable or systematic (and how repeatable and systematic). In addition, multiple instances of the patterned feature(s) may be examined to determine if the patterned feature(s) are potentially problematic. For example, the number of instances of the patterned feature(s) that are located proximate to a defect versus the number of instances of the patterned feature(s) that are not located proximate to a defect (or the total number of instances of the patterned feature(s) found) may be evaluated to determine if and how problematic the patterned feature(s) are. In other words, such evaluation may be used to quantify how prone the patterned feature(s) are to defects. Each of these steps may be performed automatically by the computer-implemented methods described herein.

In some embodiments, the method includes sampling the defects detected on the specimen for additional processing based on results of the assigning step. For instance, the defects may be sampled such that at least some defects from each of the bins into which defects were assigned are reviewed. In another instance, the defects may be sampled more heavily from regions or regions of interest in the device design that are identified as being potentially more problematic as described above. Sampling the defects for review or any other processing known in the art may be performed automatically by the computer-implemented methods described herein.

Information about which portions of the device design are potentially problematic may be used to alter the device design. For instance, the information produced by the binning methods described herein may be used to feedback to the design process the portions of the device design that should be analyzed to determine if one or more characteristics of the device design in these portions can be altered to reduce the number or the number of types of defects that are formed on additional specimens on which the device is fabricated. In this manner, the device design may be altered to reduce systematic defects. Each of these steps may be performed automatically by the computer-implemented methods described herein.

In another embodiment, the method includes identifying potentially problematic processes used to fabricate the specimen based on results of the assigning of the defects into bins. For example, as described above, the number of defects assigned to bins associated with the different regions of interest may indicate that one region of interest is more prone to defects than another region of interest. In this manner, the results of the binning step may be used to identify the region or regions of interest in the device design that are potentially more problematic (e.g., more prone to defects). In addition, information about which portions of the device design are potentially problematic may be used to identify one or more processes that may be causing the defects in the region or regions of interest. For instance, the information produced by the binning methods described herein may be used to determine if one or more parameters of the processes used to fabricate the specimen can be altered to reduce the number or the number of types of defects that are formed on additional specimens on which the device is fabricated. The processes that can be identified as potentially problematic by the methods described herein include any processes that can be used to fabricate specimens (e.g., lithography, etch, chemical-mechanical polishing, deposition, cleaning, annealing, etc.). The results of the defect binning performed by the methods and systems described herein may, therefore, be used to alter a parameter of a process or a process tool using a feedback control technique. The parameter of the process or the process tool may be altered automatically.

Often, the device design and the processes used to fabricate the specimen "interact" to produce defects on the specimen. In this manner, the method may include both altering the device design and the processes used to fabricate the specimen based on the information produced by assigning defects into bins as described herein to reduce the number of defects produced on the specimens due to the interrelated effects of design and process parameters. Each of the embodiments of the method described above may include any other step(s) described herein.

The method shown in FIG. 2 is different than the method shown in FIG. 1 in that in the method shown in FIG. 2, the test image is not compared to reference images. Instead, in the method shown in FIG. 2, two different test images are compared to each other. In this manner, all or some of the defects detected by inspection can be analyzed and grouped into different categories or bins by performing pattern matching between each other without having any predefined patterns or reference images.

In particular, the computer-implemented method shown in FIG. 2 includes comparing a first test image to a second test image. Although embodiments of this method are described with respect to a first test image and a second test image corresponding to a first defect and a second defect, respectively, it is to be understood that the method may include comparing the first test image to more than one other test image (e.g., at least two test images).

The first test image includes an image of one or more patterned features formed on the specimen proximate to a first defect detected on the specimen. In some embodiments, the first test image may also include an image of the first defect. For instance, as shown in FIG. 2, first test image 34 includes an image of first defect 36 detected on a specimen and patterned features 38 formed on the specimen proximate to first defect 36. The second test image includes an image of one or more patterned features formed on the specimen proximate to a second defect detected on the specimen. In some embodiments, the second test image includes an image of the second defect. For example, as shown in FIG. 2, second test image 40 includes an image of second defect 42 detected on a specimen and patterned features 44 formed on the specimen proximate to second defect 42.

The first and second test images may be acquired as described above. For instance, the first and second test images may be acquired at the locations of the first and second defects on the specimen, respectively. In this manner, the first and second test images may include images of the first and second defects, respectively. In a different embodiment, the first and second test images are acquired at locations on the specimen spaced from the first and second defects, respectively, at which the one or more patterned features are located and at which additional defects are not located.

Comparing the first and second test images includes determining if the one or more patterned features of the first and second test images match. For example, as shown in step 46 of the method shown in FIG. 2, patterned features 38 of first test image 34 are compared to patterned features 44 of second test image 40 to determine if patterned features 38 of first test image 34 match patterned features 44 of second test image 40. If the one or more patterned features of the first and second images match, the method includes assigning the first and second defects to the same bin. For example, if patterned features 38 of first test image 34 match patterned features 44 of second test image 40, the method includes assigning defects 36 and 42 to Bin 1.

Regardless of whether or not the one or more patterned features of the first and second test images match, the patterned features of first test image 34 and additional test images may be compared as described herein. In this manner, the defects in any of the test images that include images of one or more patterned features that match the one or more patterned features of the first test image may be assigned to the same bin as the first defect. However, as clearly shown in FIG. 2, the patterned features of first test image 34 and second test image 40 do not match. Therefore, first defect 36 and second defect 42 are not assigned to the same bin.

The first test image may be compared to third test image 48 that includes an image of patterned features 52 formed on the specimen proximate to a third defect. Third test image 48 may also include an image of third defect 50. As shown in step 54 of the method shown in FIG. 2, first test image 34 is compared to third test image 48 to determine if patterned features 38 of first test image 34 match patterned features 52 of third test image 48. If the patterned features of the first and third test images match, the method includes assigning defects 36 and 50 to the same bin. In this case, as shown in FIG. 2, the patterned features of first test image 34 and third test image 48 match. Therefore, defects 36 and 50 included in first test image 34 and third test image 48, respectively, are assigned to Bin 2. As described above, regardless of whether or not the one or more patterned features of the first and third test images match, the patterned features of first test image 34 and additional test images may be compared as described herein.

As shown in test images 34 and 48, defects 36 and 50 do not have substantially the same attributes. In particular, defects 36 and 50 have different sizes and shapes. However, these defects will be assigned to the same bin because their background contexts (e.g., patterned features 38 and 52) match. Therefore, regardless of the attributes of the defects, defects located in the same regions of interest as indicated by their background context can be assigned to the same bin. After the defects have been binned by context, they may be further separated into "sub-bins" by classifying the defects based on one or more attributes of the defects, which may be performed as described herein. Alternatively, the test images may be compared by considering the defects as part of the patterns that are matched when comparing two test images to each other. In this manner, the defects may be simultaneously separated into different bins by background context and one or more attributes of the defects. For instance, defects that appear in a contact region of interest that have the same attributes can be assigned to one bin, and defects that appear in the same contact region of interest but that have different attributes can be assigned to a different bin.

If the patterned features of first test image 34 do not match the patterned features of any other test images, the method may include assigning the first defect in first test image 34 to its own bin such that the first defect may be analyzed as described further herein. The method shown in FIG. 2 may be performed for some of the defects detected on a specimen or all of the defects detected on the specimen.

The method shown in FIG. 2 may include any other step(s) of any other method(s) described herein. For instance, in one embodiment, the method includes identifying potentially problematic portions of the design of a device being formed on the specimen based on results of the assigning step. In another embodiment, the method includes identifying potentially problematic processes used to fabricate the specimen based on results of the assigning step. In a further embodiment, the method includes identifying a sample of the defects detected on the specimen to be reviewed based on results of the assigning step. Each of these steps may be performed as described further herein.

In one embodiment, if the one or more patterned features in the first and second test images match, the method includes determining if the first and second defects are repeating defects. In some embodiments, the method includes classifying the first and second defects based on one or more attributes of the first and second defects, respectively. In a further embodiment, the method includes classifying the first and second defects based on one or more attributes of the first and second defects, respectively, and one or more attributes of the one or more patterned features proximate to the first and second defects, respectively. In some embodiments, the method includes creating a subset of the defects based on locations of the defects within a die formed on the specimen or locations of the defects on the specimen and classifying the subset based on one or more attributes of the one or more patterned features proximate to the defects within the subset. In a further embodiment, the method includes using the one or more patterned features proximate to the defects in a simulation of design data for a device being formed on the specimen to classify the defects. Each of these steps may be performed as described further herein.

In another embodiment, the method is performed during inspection of the specimen. In an alternative embodiment, the method is performed using the first and second test images acquired during inspection of the specimen. In an additional embodiment, the method is performed during review of the defects. In yet another embodiment, the method includes performing the method in conjunction with statistical methods performed on the first and second test images. Each of these steps may be performed as described further herein. In addition, each of the embodiments of the method shown in FIG. 2 has all of the advantages of the method shown in FIG. 1 described further above.

Figure 3:
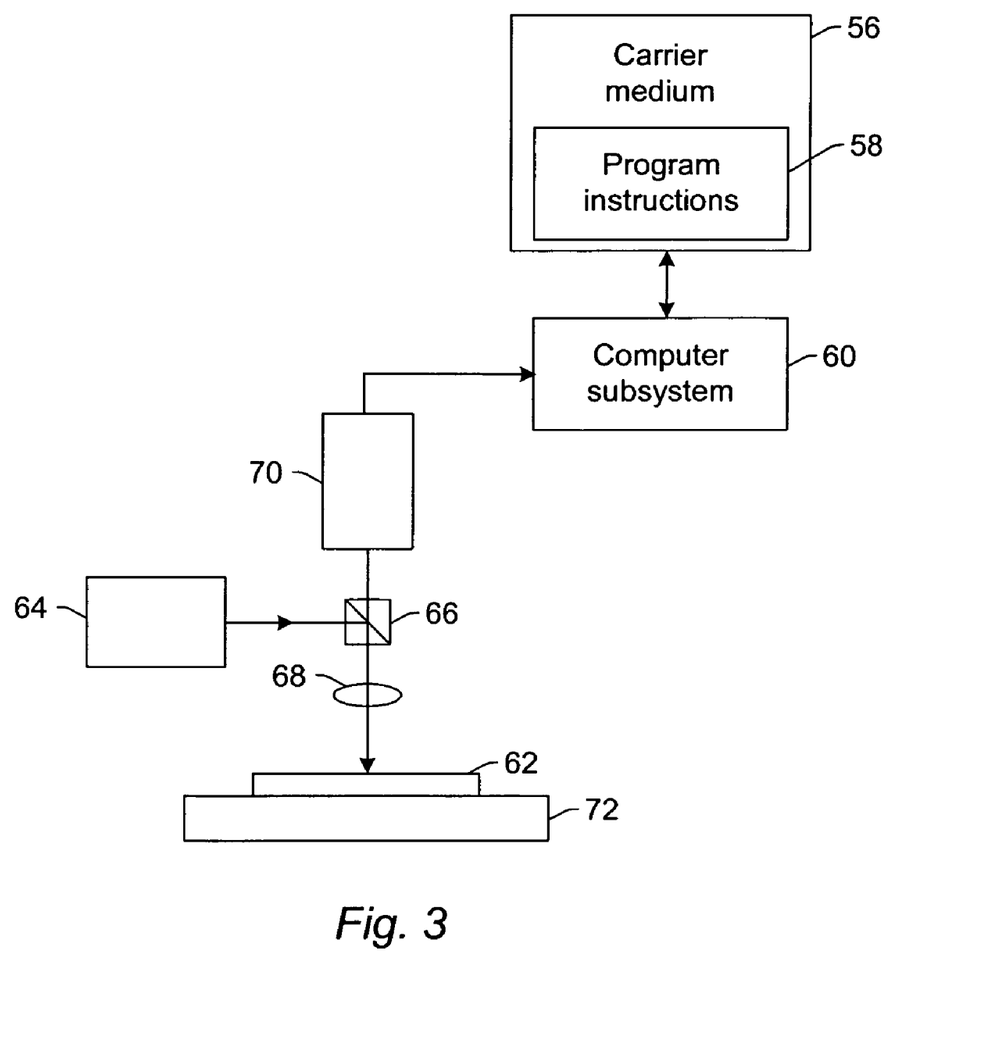
FIG. 3 is a schematic diagram illustrating a cross-sectional view of one embodiment of a carrier medium and a system configured to bin defects detected on a specimen.

FIG. 3 illustrates one embodiment of carrier medium 56. Carrier medium 56 includes program instructions 58 executable on a computer system (e.g., computer subsystem 60) for performing a method for binning defects detected on specimen 62. The method includes comparing a test image to reference images, which may be performed as described above. The test image includes an image of one or more patterned features formed on the specimen proximate to a defect detected on the specimen. The reference images include images of one or more patterned features associated with different regions of interest within a device being formed on the specimen. In one embodiment, the different regions of interest include regions of the device in which DOI may be present. In another embodiment, the different regions of interest do not include regions of the device in which only nuisance defects may be present. The test and reference images may be further configured and acquired as described herein.

If the one or more patterned features of the test image match the one or more patterned features of one of the reference images, the method includes assigning the defect to a bin corresponding to the region of interest associated with the one reference image, which may be performed as described herein. The method for which the program instructions are executable may include any other step(s) described herein.

For example, in one embodiment, if the one or more patterned features of the test image do not match the one or more patterned features of any of the reference images, the method includes identifying the defect as a nuisance defect. In another embodiment, the method includes identifying the regions of interest containing potentially problematic portions of the design of the device based on results of the assigning step. In a further embodiment, the method includes identifying potentially problematic processes used to fabricate the specimen based on results of the assigning step. Each of these steps may be performed as described further herein.

In an additional embodiment, the method includes classifying the defect based on one or more attributes of the defect. In another embodiment, the method includes classifying the defect based on one or more attributes of the defect and one or more attributes of the one or more patterned features formed on the specimen proximate to the defect. Each of the steps described above may be performed as described further herein. Each of the embodiments of the method described above has all of the advantages of the methods described herein.

The program instructions may also or alternatively be configured to perform other embodiments of a method for binning defects detected on specimen 62 described herein. For instance, in one embodiment, the method for which the program instructions are executable includes comparing a first test image to a second test image, which may be performed as described herein. The first test image includes an image of one or more patterned features formed on the specimen proximate to a first defect detected on the specimen. The second test image includes an image of one or more patterned features formed on the specimen proximate to a second defect detected on the specimen. The first and second test images may be further configured and acquired as described herein. If the one or more patterned features in the first and second test images match, the method includes assigning the first and second defects to the same bin. This method for which the program instructions are executable may include any other step(s) described herein.

For example, in one embodiment, the method includes identifying potentially problematic areas of the design of a device being formed on the specimen based on results of the assigning step. In another embodiment, the method includes identifying potentially problematic processes used to fabricate the specimen based on results of the assigning step. Each of these steps may be performed as described further herein.

In an additional embodiment, the method includes classifying the first and second defects based on one or more attributes of the first and second defects, respectively. In a further embodiment, the method includes classifying the first and second defects based on one or more attributes of the first and second defects, respectively, and one or more attributes of the one or more patterned features proximate to the first and second defects, respectively. Each of the steps described above may be performed as described further herein. Each of the embodiments of the method described above has all of the advantages of the methods described herein.

The carrier medium may be a transmission medium such as a wire, cable, or wireless transmission link. The carrier medium may also be a storage medium such as a read-only memory, a random access memory, a magnetic or image acquisition disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

The computer system and computer subsystem 60 may take various forms, including a personal computer system, mainframe computer system, workstation, image computer or any other device known in the art. In general, the term "computer system" may be broadly defined to encompass any device having one or more processors, which executes instructions from a memory medium.

FIG. 3 also illustrates one embodiment of a system configured to bin defects detected on a specimen. The system shown in FIG. 3 includes an inspection subsystem. It is noted that FIG. 3 is provided herein to generally illustrate one embodiment of a configuration for an inspection subsystem that may be included in the system. Obviously, the system configuration described herein may be altered to optimize the performance of the system as is normally performed when designing a commercial inspection system. In addition, the systems described herein may be implemented using an existing inspection subsystem (e.g., by adding functionality described herein to an existing inspection system). For some such systems, the defect binning methods described herein may be provided as optional functionality of the system (e.g., in addition to other functionality of the system). Alternatively, the system described herein may be designed "from scratch" to provide a completely new system.

The inspection subsystem is configured to acquire a test image of one or more patterned features (not shown in FIG. 3) formed on specimen 62 proximate to a defect (not shown in FIG. 3) detected on the specimen. The inspection subsystem includes light source 64. Light source 64 may include any appropriate light source known in the art. Light generated by light source 64 is directed to beam splitter 66. Beam splitter 66 is configured to direct the light from light source 64 to objective 68. Beam splitter 66 may include any appropriate beam splitter known in the art. Objective 68 is configured to focus the light from beam splitter 66 to the specimen. Although objective 68 is shown in FIG. 3 as a single refractive optical element, it is to be understood that objective 68 may include one or more refractive optical elements and/or one or more reflective optical elements.

As shown in FIG. 3, the inspection subsystem is configured to illuminate the specimen by directing the light to the specimen at a substantially normal angle of incidence. However, in other embodiments (not shown), the inspection subsystem may be configured to illuminate the specimen by directing the light to the specimen at an oblique angle of incidence.

In the embodiment shown in FIG. 3, objective 68 is configured to collect light reflected from the specimen. Light collected by objective 68 passes through beam splitter 66 and is directed to detector 70 of the inspection subsystem. Detector 70 is configured to detect light transmitted by beam splitter 66. The inspection subsystem may include one or more optical components (not shown) such as a focusing or imaging lens disposed in the optical path between beam splitter 66 and detector 70. Detector 70 is configured to generate images (e.g., test images) responsive to the light reflected from the specimen. Detector 70 may be any appropriate detector known in the art such as a charge coupled device (CCD) and a time delay integration (TDI) camera.

The inspection subsystem shown in FIG. 3 is, therefore, configured to generate images responsive to light specularly reflected from the specimen. Therefore, the inspection subsystem is configured as a bright field (BF) imaging based inspection subsystem. However, in other embodiments, the inspection subsystem may be configured as a dark field (DF) imaging based inspection subsystem. In a further embodiment, the optical inspection subsystem may be replaced by an electron beam inspection subsystem (not shown). The electron beam inspection subsystem may be configured to generate the test images described herein. Examples of commercially available electron beam inspection subsystems that may be included in the system of FIG. 3 include the electron beam subsystems that are included in the eDR5000 system, the eCD-1 system, and the eS25 and eS30 systems, which are commercially available from KLA-Tencor.

In some embodiments, the inspection subsystem is also configured to acquire the reference images. As described above, each reference image may correspond to a different region of interest. Therefore, a reference image may be acquired for each different region of interest within the device being formed on the specimen.

In one embodiment, the inspection subsystem may be configured to acquire the reference images by imaging a specimen on which the regions of interest are formed. For instance, the system may include computer subsystem 60, which may be configured to estimate a location of a region of interest on a specimen based on the design of the device. The computer subsystem may be configured to position the field of view of the inspection subsystem at the estimated location. Alternatively, the computer subsystem may be configured to provide the estimated location to the inspection subsystem, which may be configured to position its field of view above the estimated location. The inspection subsystem may then acquire an image at the estimated location. To verify that the image has been acquired at a location within the region of interest, the computer subsystem may be configured to compare the image to the design as described above. If one or more patterned features appear in both the image and the design for the region of interest, then the computer subsystem may verify the image as being acquired in the region of interest. In addition, the reference images may include images of the regions of interest in which no defects are present. For instance, once the image has been acquired by the inspection subsystem at the estimated location, the computer subsystem may use a defect detection algorithm or method to determine if a defect is present in the image. If a defect is present in the image, the inspection subsystem may acquire a different image at another location in the region of interest, and the steps described above may be performed until a suitable reference image has been acquired.

In addition, the inspection subsystem and the computer subsystem may be configured to acquire more than one reference image for each region of interest as described above. Therefore, in some embodiments, the computer subsystem may be configured to compare a test image to multiple reference images for each region of interest.

In another embodiment, the reference images may be acquired by simulation. For instance, the computer subsystem may be configured to generate a simulated image of each of the regions of interest using the design data as input. The simulated images may be configured as described above. The computer subsystem may also be configured to generate the simulated images using the design data as input to one or more models (e.g., a lithography model, an etch model, a chemical-mechanical polishing model, etc.) for the processes that will be performed on the specimen prior to inspection. Such simulations may be performed using any suitable method or software known in the art such as PROLITH.

The system may be configured to acquire the reference images in the embodiments described above manually, automatically, or semi-automatically (e.g., user-assisted). In addition, the system may be configured to acquire the reference images by generating the reference images as described above or to acquire the reference images from a different system. The system described herein may be configured to acquire the reference images from another system via a transmission medium coupling the two systems (e.g., a data link) or from a storage medium in which the reference images are stored by the other system and which can be accessed by both systems. Furthermore, the system may be configured to acquire the reference images as described above once for each level of the design that will be inspected during the manufacture of the device. However, the system may be configured to acquire additional reference images periodically after initial set up (e.g., during periodic maintenance or calibration) such that variations in the reference images and the test images over time do not decrease the accuracy of the method.

Detector 70 is coupled to computer subsystem 60. Computer subsystem 60 may be coupled to detector 70 such that the computer subsystem can receive the test images generated by the detector. For example, computer subsystem 60 may be coupled to the detector by a transmission medium (not shown) or an electronic component (not shown) interposed between the detector and the computer subsystem. The transmission medium and the electronic component may include any suitable such medium and component known in the art.

Computer subsystem 60 may be configured to detect defects on the specimen using the test images or other images acquired by the inspection subsystem. Computer subsystem 60 may be configured to use any suitable method and/or algorithm known in the art to detect defects on the specimen using the test images. Computer subsystem 60 may also be configured to perform one or more embodiments of the methods described herein for binning defects detected on specimen 62.

The system shown in FIG. 3 also includes carrier medium 56 and program instructions 58. The carrier medium and the program instructions may be configured as described above. In addition, the carrier medium may include program instructions executable on a computer system of any other inspection system that can be configured as described herein.

The system may also include stage 72 on which specimen 62 may be disposed during inspection. Stage 72 may include any suitable mechanical or robotic assembly known in the art. Scanning of light across the specimen may be performed in any manner known in the art. The system shown in FIG. 3 may be further configured as described herein (e.g., according to any other embodiments described herein).

Further modifications and alternative embodiments of various aspects of the invention may be apparent to those skilled in the art in view of this description. For example, methods and systems for binning defects detected on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for binning defects detected on a specimen, comprising:
    performing on a computer processor the following steps:
    comparing a test image to reference images, wherein the test image comprises an image of one or more patterned features formed on the specimen proximate to a defect detected on the specimen, and wherein the reference images comprise images of one or more patterned features associated with different regions of interest within a device being formed on the specimen;
    and if the one or more patterned features of the test image match the one or more patterned features of one of the reference images, assigning the defect to a bin corresponding to the region of interest associated with the one of the reference images.

2. The method of claim 1, wherein the different regions of interest comprise regions of the device in which defects of interest may be present.

3. The method of claim 1, wherein the different regions of interest do not comprise regions of the device in which nuisance defects may be present.

4. The method of claim 1, wherein if the one or more patterned features of the test image do not match the one or more patterned features of any of the reference images, the method further comprises identifying the defect as a nuisance defect.

5. The method of claim 1, wherein the reference images further comprise images of one or more patterned features associated with regions of the device in which nuisance defects may be present, and wherein if the one or more patterned features of the test image match the one or more patterned features of one of the reference images associated with the regions of the device in which nuisance defects may be present, the method further comprises identifying the defect as a nuisance defect.

6. The method of claim 5, wherein if the one or more patterned features of the test image do not match the one or more patterned features of any of the reference images, the method further comprises identifying the defect as a nuisance defect.

7. The method of claim 1, wherein the test image further comprises an image of the defect.

8. The method of claim 1, wherein the test image is acquired at a location on the specimen spaced from the defect at which the one or more patterned features are located and at which additional defects are not located.

9. The method of claim 1, further comprising identifying the regions of interest containing potentially problematic portions of the design of the device based on results of said assigning.

10. The method of claim 1, further comprising identifying potentially problematic processes used to fabricate the specimen based on results of said assigning.

11. The method of claim 1, wherein if the one or more patterned features of the test image match the one or more patterned features of one of the reference images, the method further comprises determining if the defect is a repeating defect.

12. The method of claim 1, further comprising classifying the defect based on one or more attributes of the defect.

13. The method of claim 1, further comprising classifying the defect based on one or more attributes of the defect and one or more attributes of the one or more patterned features formed on the specimen proximate to the defect.

14. The method of claim 1, further comprising sampling the defects detected on the specimen for additional processing based on results of said assigning.

15. The method of claim 1, further comprising locating additional instances of the one or more patterned features proximate to the defect in the device.

16. The method of claim 1, further comprising locating additional instances of the one or more patterned features proximate to the defect on the specimen.

17. The method of claim 1, further comprising acquiring the test image by optical inspection.

18. The method of claim 1, further comprising acquiring the test image by electron beam inspection.

19. The method of claim 1, further comprising acquiring the test image by electron beam review.

20. The method of claim 1, further comprising acquiring the test image by an aerial image projection technique.

21. The method of claim 1, wherein method is performed during inspection of the specimen.

22. The method of claim 1, wherein the method is performed using the test image acquired during inspection of the specimen.

23. The method of claim 1, wherein the method is performed during review of the defects.

24. The method of claim 1, further comprising acquiring the test image by analyzing design data for the device being formed on the specimen.

25. The method of claim 1, further comprising performing the method in conjunction with statistical methods performed on the test image.

26. A computer-implemented method for binning defects detected on a specimen, comprising:
    performing on a computer processor the following steps:

comparing a first test image to a second test image, wherein the first test image comprises an image of one or more patterned features formed on the specimen proximate to a first defect detected on the specimen, and wherein the second test image comprises an image of one or more patterned features formed on the specimen proximate to a second defect detected on the specimen;

and if the one or more patterned features in the first and second test images match, assigning the first and second defects to the same bin.

27. The method of claim 26, wherein the first and second test images further comprise images of the first and second defects, respectively.

28. The method of claim 26, wherein the first and second test images are acquired at locations on the specimen spaced from the first and second defects, respectively, at which the one or more patterned features are located and at which additional defects are not located.

29. The method of claim 26, further comprising identifying potentially problematic portions of the design of a device being formed on the specimen based on results of said assigning.

30. The method of claim 26, further comprising identifying potentially problematic processes used to fabricate the specimen based on results of said assigning.

31. The method of claim 26, further comprising identifying a sample of the defects detected on the specimen to be reviewed based on results of the assigning step.

32. The method of claim 26, wherein if the one or more patterned features in the first and second test images match, the method further comprises determining if the first and second defects are repeating defects.

33. The method of claim 26, further comprising classifying the first and second defects based on one or more attributes of the first and second defects, respectively.

34. The method of claim 26, further comprising classifying the first and second defects based on one or more attributes of the first and second defects, respectively, and one or more attributes of the one or more patterned features proximate to the first and second defects, respectively.

35. The method of claim 26, further comprising creating a subset of the defects based on locations of the defects within a die formed on the specimen or locations of the defects on the specimen and classifying the subset based on one or more attributes of the one or more patterned features proximate to the defects within the subset.

36. The method of claim 26, further comprising using the one or more patterned features proximate to the defects in a simulation of design data for a device being formed on the specimen to classify the defects.

37. The method of claim 26, further comprising acquiring the first and second test images by optical inspection.

38. The method of claim 26, further comprising acquiring the first and second test images by electron beam inspection.

39. The method of claim 26, further comprising acquiring the first and second test images by electron beam review.

40. The method of claim 26, further comprising acquiring the first and second test images by an aerial image projection technique.

41. The method of claim 26, wherein the method is performed during inspection of the specimen.

42. The method of claim 26, wherein the method is performed using the first and second test images acquired during inspection of the specimen.

43. The method of claim 26, wherein the method is performed during review of the defects.

44. The method of claim 26, further comprising acquiring the first and second test images by analyzing design data for the specimen.

45. The method of claim 26, further comprising performing the method in conjunction with statistical methods performed on the first and second test images.

* * * * *